US 10,314,676 B2

(12) United States Patent
Wada et al.

(10) Patent No.: US 10,314,676 B2
(45) Date of Patent: Jun. 11, 2019

(54) ORAL CLEANING DEVICE

(71) Applicant: SUNSTAR INC., Takatsuki-shi (JP)

(72) Inventors: Yukinori Wada, Takatsuki (JP);
Masahiro Nishiura, Takatsuki (JP)

(73) Assignee: SUNSTAR INC., Takatsuki-shi (JP)

(*) Notice: Subject to any disclaimer, the term of this patent is extended or adjusted under 35 U.S.C. 154(b) by 426 days.

(21) Appl. No.: 14/441,004

(22) PCT Filed: Oct. 24, 2013

(86) PCT No.: PCT/JP2013/078784
§ 371 (c)(1),
(2) Date: May 6, 2015

(87) PCT Pub. No.: WO2014/073382
PCT Pub. Date: May 15, 2014

(65) Prior Publication Data
US 2015/0282908 A1    Oct. 8, 2015

(30) Foreign Application Priority Data
Nov. 8, 2012  (JP) .................................. 2012-246007

(51) Int. Cl.
A61C 17/02       (2006.01)
A61C 17/028      (2006.01)

(52) U.S. Cl.
CPC ........ A61C 17/0202 (2013.01); A61C 17/028 (2013.01)

(58) Field of Classification Search
CPC .............. A61C 17/0202; A61C 17/028; A61C 17/0217; B05B 12/06; B05B 7/2437; E03C 1/084

(Continued)

(56) References Cited
U.S. PATENT DOCUMENTS 5,615,695 A * 4/1997 Chambers ............. B08B 9/0321
                                                134/102.1
5,820,373 A * 10/1998 Okano ................... A61C 17/02
                                                433/216

(Continued)

FOREIGN PATENT DOCUMENTS
JP     S57-43739      3/1982
JP     H05-161663     6/1993

(Continued)

OTHER PUBLICATIONS
International Search Report for International Application No. PCT/JP2013/078784 dated Jan. 21, 2014.

Primary Examiner — Matthew M Nelson
(74) Attorney, Agent, or Firm — Kratz, Quintos & Hanson, LLP

(57) ABSTRACT

Provided is an oral cleaning device capable of ensuring a sufficient ejection pressure for a cleaning liquid while employing a small and low-cost electric air pump with a low output. An oral cleaning device is provided with an airtightly closable cleaning liquid tank 2 which stores a cleaning liquid, a cleaning liquid supply passage 24 which has an ejection port 4a for ejecting the cleaning liquid into the oral cavity on one end and an introduction port 23a open inside the bottom part of the cleaning liquid tank 2 on the other end, and an electric air pump 44 which supplies air into the cleaning liquid tank 2 to pressurize the inside of the cleaning liquid tank 2. The cleaning liquid inside the cleaning liquid tank 2 is supplied to the ejection port 4a through the cleaning liquid supply passage 24 by air pressure inside the cleaning liquid tank 2. An air introduction hole 71 which is open on the midway part of the cleaning liquid supply passage 24 is provided and part of the air supplied to the cleaning liquid tank 2 from the air pump 44 is supplied to the cleaning liquid (Continued)

supply passage 24 through the air introduction hole 71 to eject the cleaning liquid in a pulsatile manner from the ejection port 4*a*.

7 Claims, 13 Drawing Sheets

(58) Field of Classification Search
USPC ....... 433/80, 89; 239/101, 419.5, 428.5, 369
See application file for complete search history.

(56) References Cited

U.S. PATENT DOCUMENTS

| | | | |
|---|---|---|---|
| 8,317,514 B2* | 11/2012 | Weill | A61L 12/02 |
| | | | 433/80 |
| 2006/0078844 A1* | 4/2006 | Goldman | A61C 1/0084 |
| | | | 433/80 |
| 2011/0207078 A1* | 8/2011 | Johnson | A61C 17/028 |
| | | | 433/88 |
| 2011/0253805 A1 | 10/2011 | Lee | |

FOREIGN PATENT DOCUMENTS

| | | |
|---|---|---|
| JP | H11-128252 | 5/1999 |
| JP | 2002-263122 A1 | 9/2002 |
| JP | 2007-190291 A1 | 8/2007 |
| JP | 4120621 B2 | 7/2008 |

\* cited by examiner

[Fig. 1]
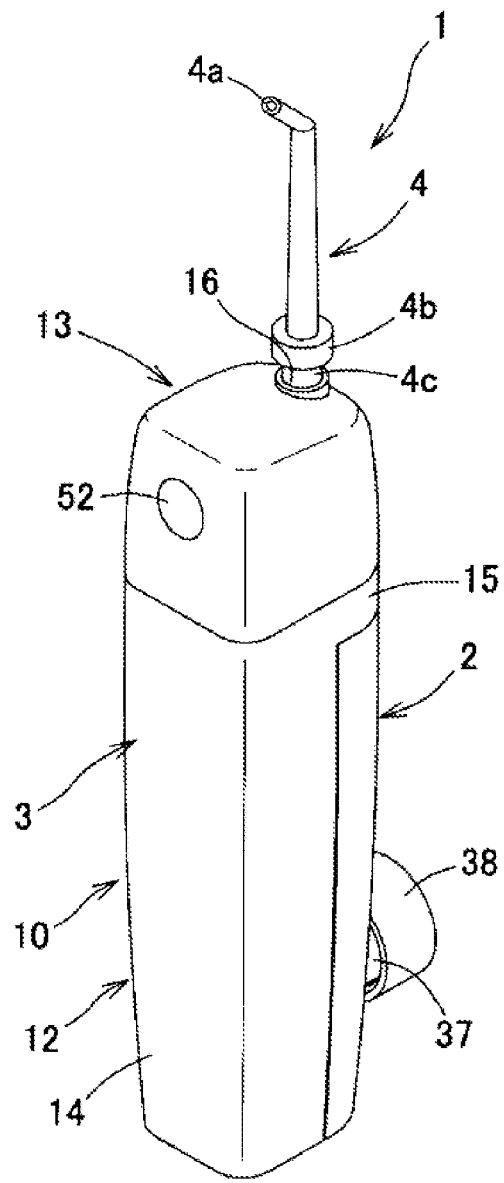

[Fig. 2]
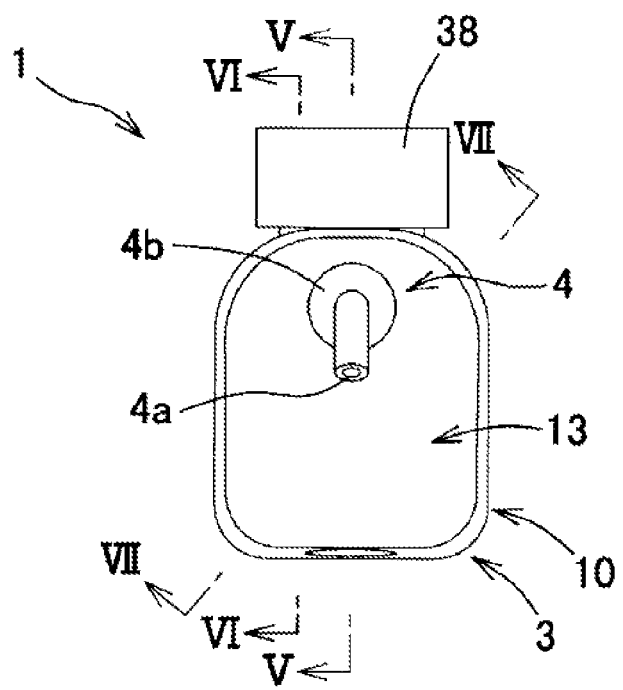

[Fig. 3]
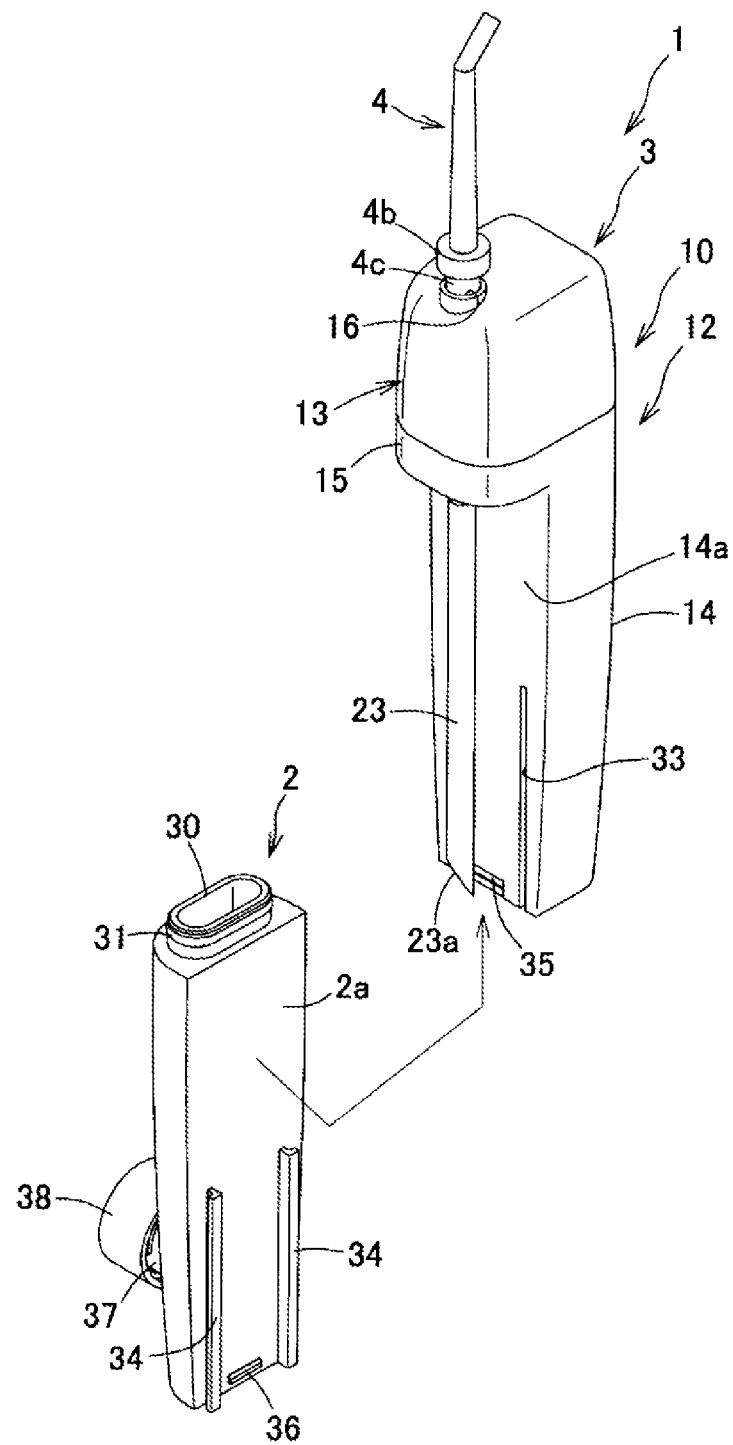

[Fig. 4]
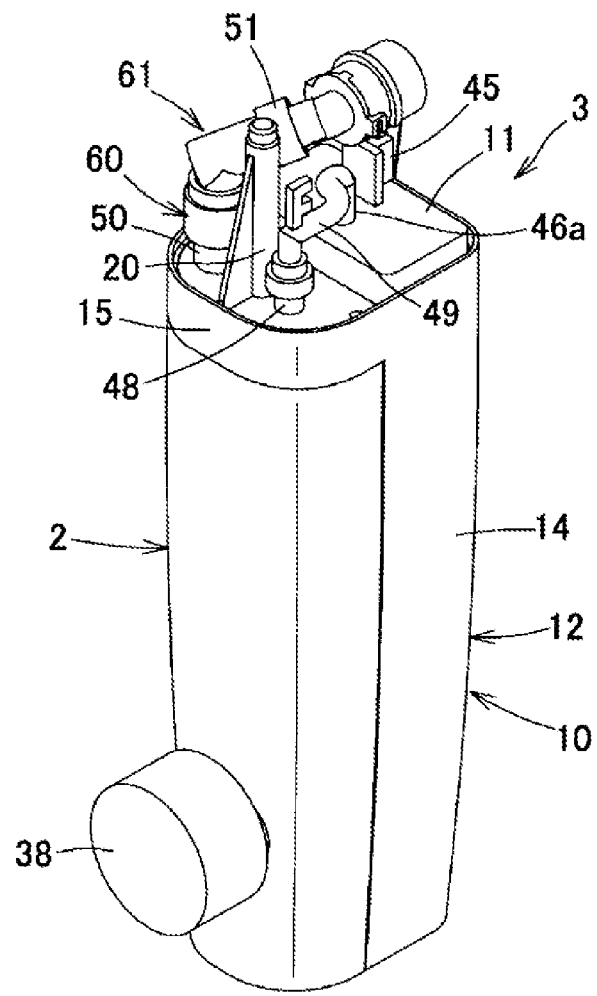

[Fig. 5]
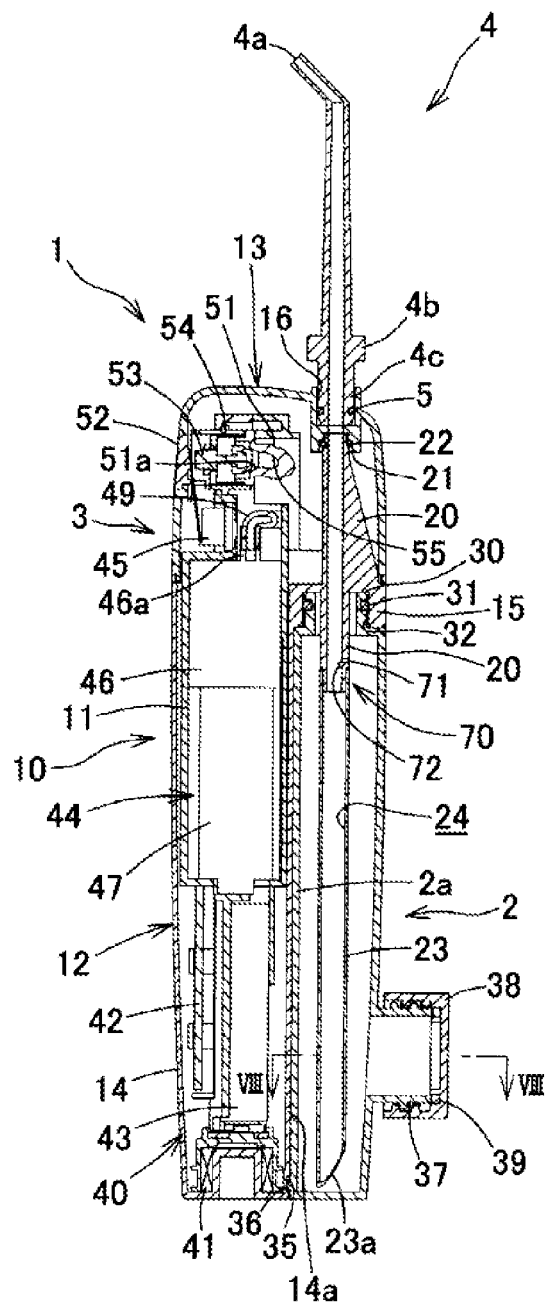

[Fig. 6]
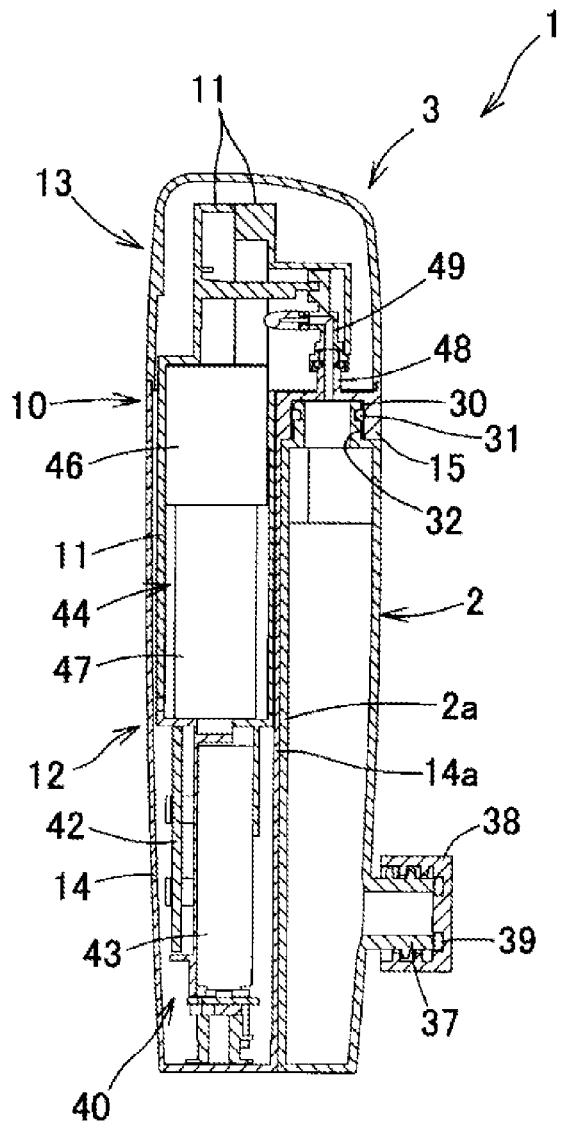

[Fig. 7]
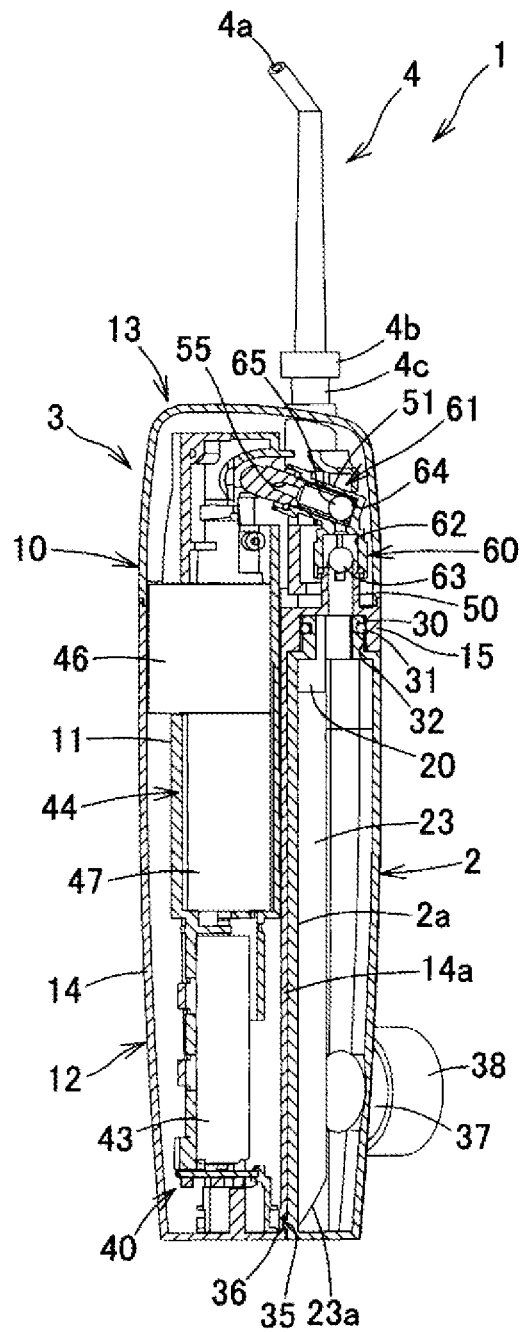

[Fig. 8]
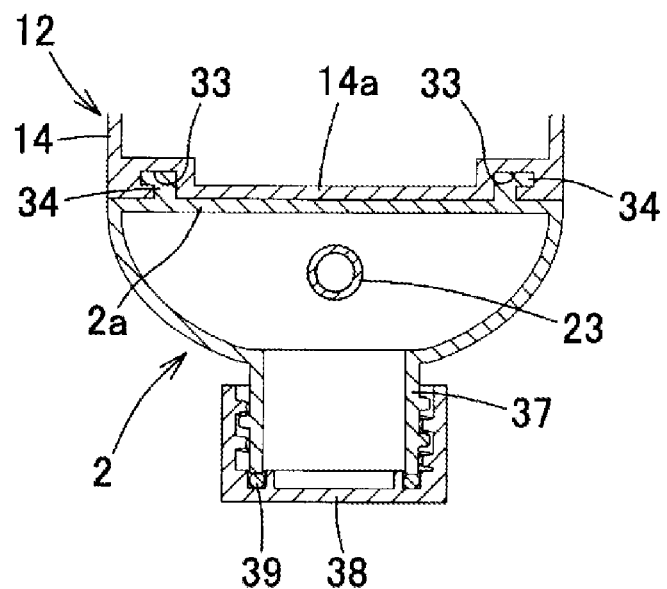
[Fig. 9]
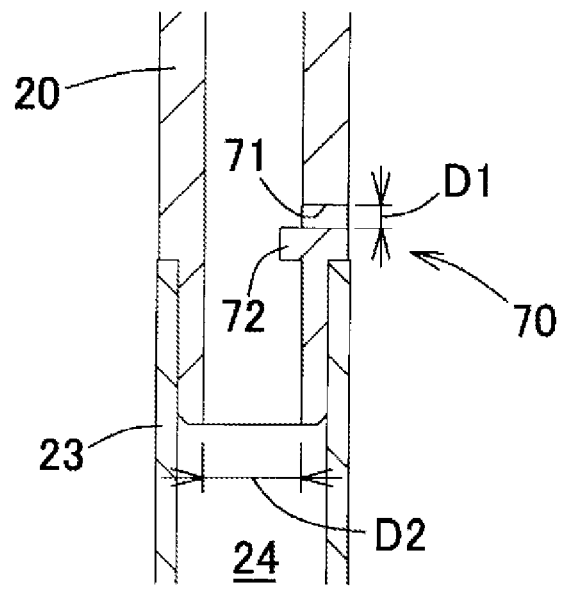

[Fig. 10]
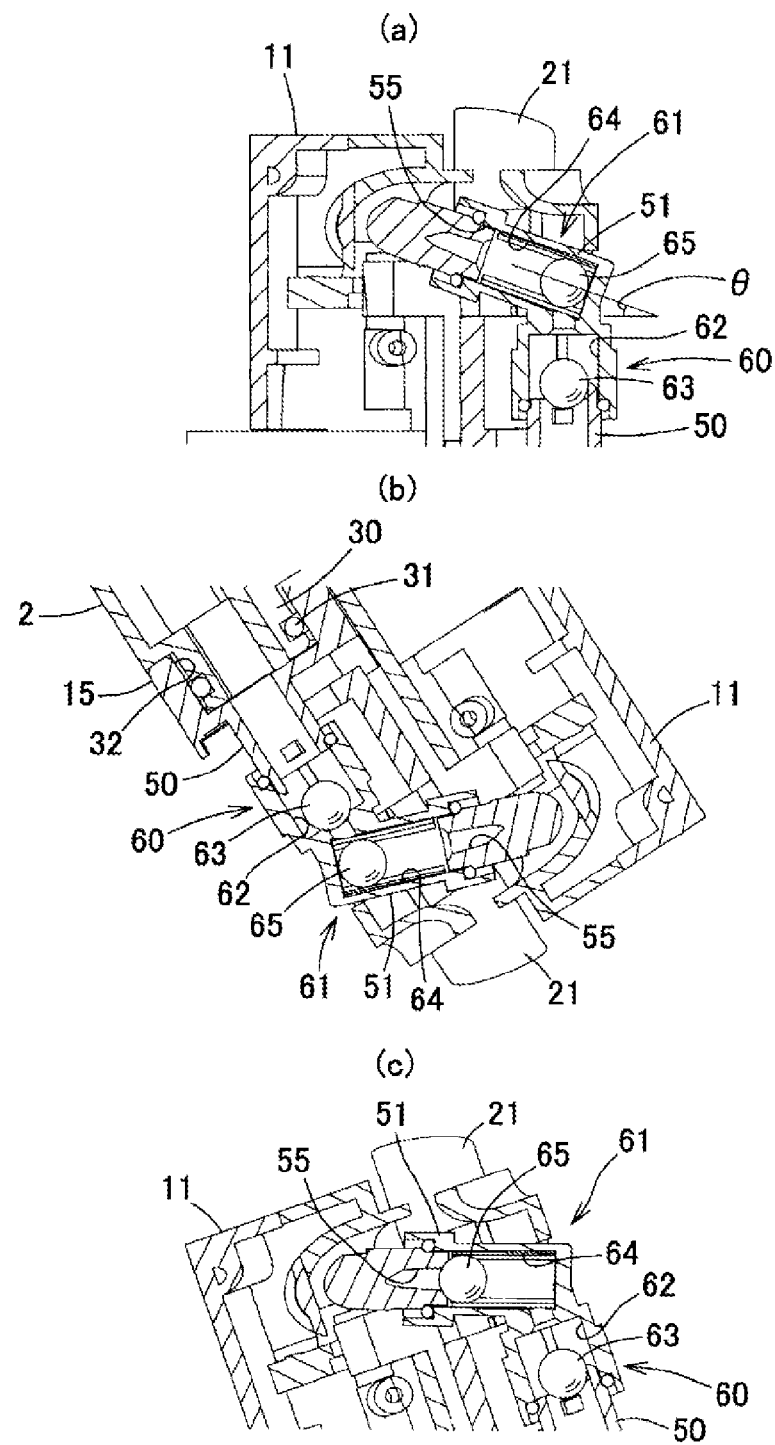

[Fig. 11]
(a)
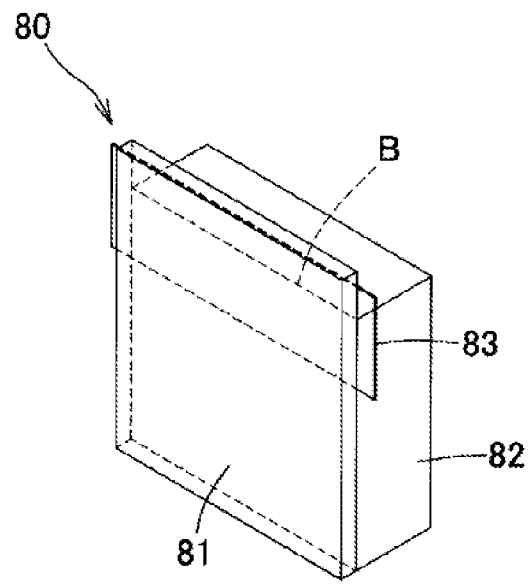
(b)
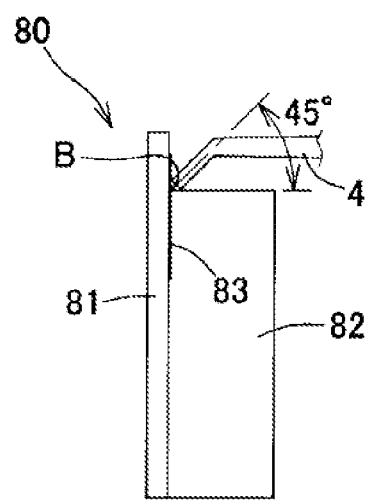

[Fig. 12]
(Flow rate: 1.1 L/min)
(a) Pulsatile ejection　　　　　　　　(b) Steady ejection
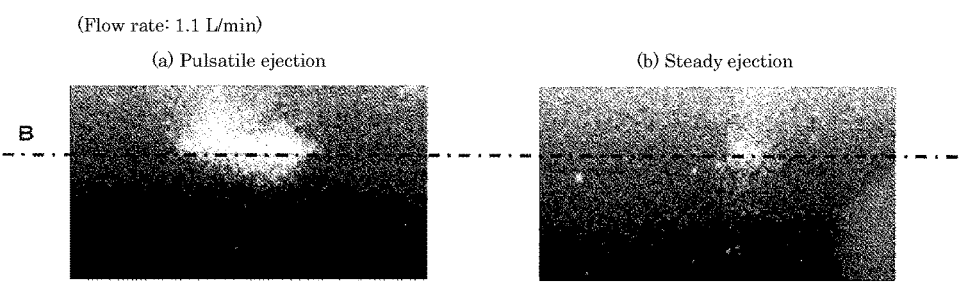
[Fig. 13]
(Flow rate: 2.1 L/min)
(a) Pulsatile ejection　　　　　　　　(b) Steady ejection
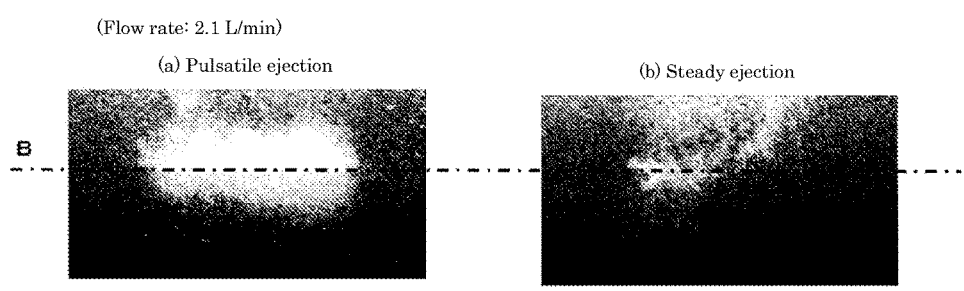
[Fig. 14]
(Flow rate: 3.9 L/min)
(a) Pulsatile ejection　　　　　　　　(b) Steady ejection
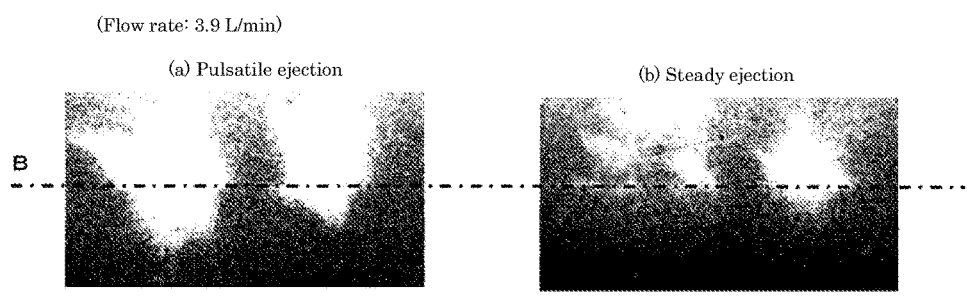

[Fig. 15]
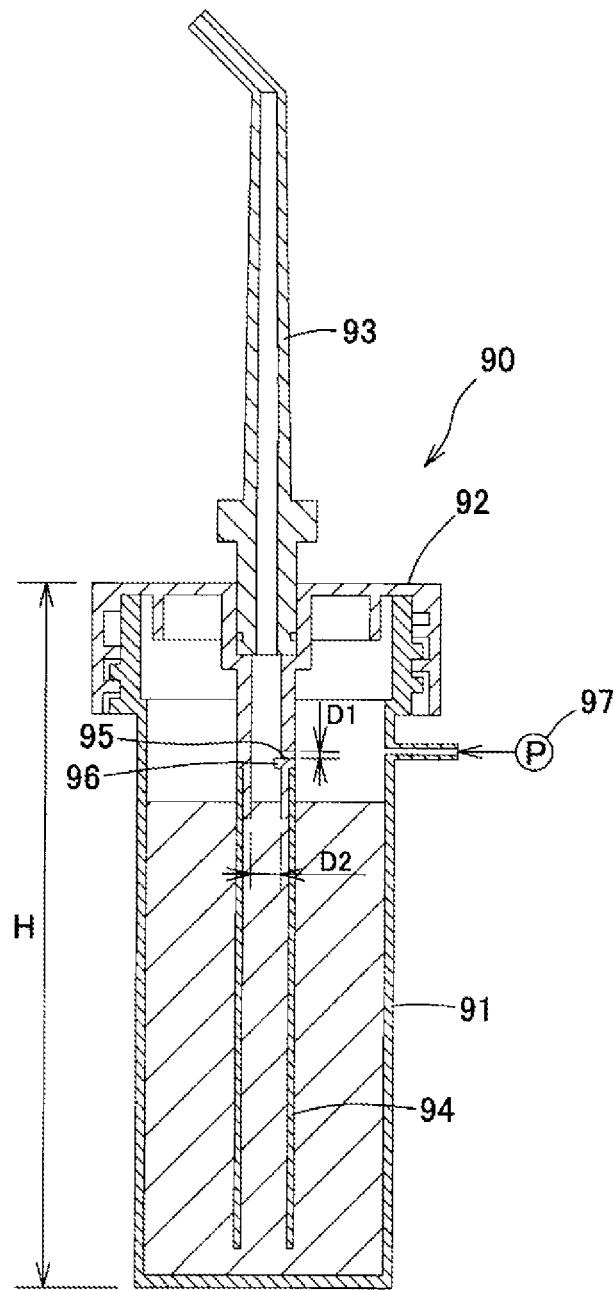

[Fig. 16]
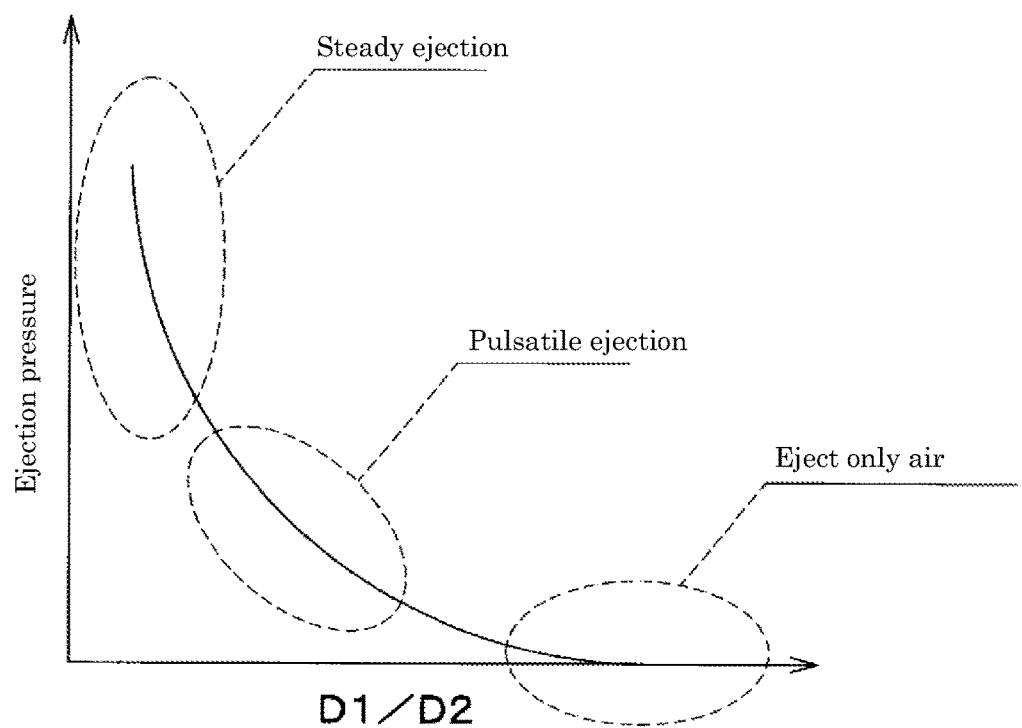

ORAL CLEANING DEVICE

TECHNICAL FIELD

The present invention relates to an oral cleaning device capable of cleaning the oral cavity with a cleaning liquid ejected from a nozzle.

BACKGROUND ART

There has been proposed, as an oral cleaning device capable of cleaning the oral cavity with a cleaning liquid ejected from a nozzle, a water flow type oral cleaning device which is provided with a pump capable of ejecting a cleaning liquid by the linear reciprocating motion of a piston, pump driving means which drives the piston, and an ejection nozzle for the cleaning liquid, and capable of efficiently cleaning, for example, interdental spaces and periodontal pockets with the cleaning liquid by jetting the cleaning liquid from the nozzle (refer to Patent Documents 1 and 2, for example).

In oral cleaning devices described in Patent Documents 1 and 2, a cleaning liquid can be ejected from a nozzle by the reciprocating motion of a piston. For example, the cleaning liquid is filled into a cylinder when the piston moves forward and the cleaning liquid inside the cylinder is ejected from the nozzle when the piston moves backward. Accordingly, the cleaning liquid is intermittently ejected from the nozzle so that the cleaning liquid pulsates. Thus, these oral cleaning devices have the following advantage. When periodontal pockets are cleaned, a cleaning liquid supplied into the periodontal pockets is discharged from the periodontal pockets between ejection operations of the cleaning liquid, that is, when the ejection of the cleaning liquid is stopped. Thus, it is possible to reduce collision of the cleaning liquid inside the periodontal pockets to thereby allow a kinetic energy of the cleaning liquid when ejected from the nozzle to efficiently act on the periodontal pockets, compared to a case in which a cleaning liquid is continuously ejected from the nozzle without changing the flow rate. As a result, the periodontal pockets can be effectively cleaned.

Further, there has also been proposed an oral cleaning device which is configured in such a manner that an air pump for feeding air is disposed on a cleaning liquid supply passage on the downstream side with respect to a piston type pump to mix air into a cleaning liquid ejected from a nozzle so that a touch feeling caused by the cleaning liquid to gums can be softened and a comfortable feeling that cannot be obtained only by the cleaning liquid can be obtained (refer to Patent Document 3, for example).

On the other hand, there has also been proposed an oral cleaner which is configured to eject a cleaning liquid by a manual air pump (refer to Patent Document 4, for example). In this oral cleaner, an impeller which is rotated by water pressure of a cleaning liquid is disposed on the midway part of a cleaning liquid supply passage leading from a cleaning liquid tank to a nozzle to pulsate the cleaning liquid ejected from the nozzle to thereby improve the cleaning effect.

CITATION LIST

Patent Literatures

Patent Document 1: JP-A No. H11-128252
Patent Document 2: JP-A No. H05-161663
Patent Document 3: Japanese Patent No. 4120621
Patent Document 4: JP-A No. 2002-263122

SUMMARY OF INVENTION

Technical Problem

The inventions described in Patent Documents 1 to 3 have the following problems. Specifically, since a cleaning liquid is directly pressurized by the piston to eject the cleaning liquid from the nozzle, a sufficient ejection pressure cannot be obtained without employing pump driving means with a high output. Further, although a stationary type oral cleaning device which is driven by an AC power source is capable of obtaining a sufficient ejection pressure, a handy type small oral cleaning device which is driven by a battery obtains only a low ejection pressure, which results in a reduction in the cleaning power.

Further, the invention described in Patent Document 3 has another problem. Specifically, since the oral cleaning device of Patent Document 3 is provided with both the piston type pump and the air pump, the manufacturing cost of the oral cleaning device increases, and large harsh noise is generated when both the pumps are driven.

The oral cleaner described in Patent Document 4 has the following problems. Specifically, since the oral cleaner of Patent Document 4 uses the manual air pump, it is necessary to operate the air pump by one hand and, at the same time, operate the nozzle by the other hand. Thus, it is not possible to concentrate on cleaning of the oral cavity. Further, when the operation force to the air pump is weak, the cleaning liquid ejected from the nozzle does not pulsate. On the other hand, when the operation force to the air pump is strong, the cleaning liquid ejected from the nozzle may be atomized. Thus, it is difficult to maintain an optimal ejection state.

An object of the present invention is to provide an oral cleaning device capable of ensuring a sufficient ejection pressure for a cleaning liquid while employing a small and low-cost electric air pump with a low output.

Solution to Problem

An oral cleaning device according to the present invention is provided with an air-tightly closable cleaning liquid tank which stores a cleaning liquid, a cleaning liquid supply passage which has an ejection port for ejecting the cleaning liquid into the oral cavity on one end and an introduction port open inside a bottom part of the cleaning liquid tank on the other end, and an electric air pump which supplies air into the cleaning liquid tank to pressurize the inside of the cleaning liquid tank, wherein the cleaning liquid inside the cleaning liquid tank is supplied to the ejection port through the cleaning liquid supply passage by air pressure inside the cleaning liquid tank.

In this oral cleaning device, air is supplied into the cleaning liquid tank by the electric air pump to pressurize the inside of the cleaning liquid tank, and the cleaning liquid inside the cleaning liquid tank is thereby supplied to the ejection port through the cleaning liquid supply passage by air pressure inside the cleaning liquid tank. Accordingly, the oral cavity can be cleaned by the cleaning liquid ejected from the ejection port. Since the cleaning liquid is ejected by the air pump in this manner, it is possible to reduce the load on driving means such as a motor in the air pump and ensure a sufficient ejection pressure for the cleaning liquid while employing a small and low-cost air pump with a low output, compared to the case in which a cleaning liquid is ejected by directly pressurizing the cleaning liquid by the piston pump as in the inventions described in Patent Documents 1 to 3. Therefore, the present invention is preferably applied to a handy type small oral cleaning device which has difficulty in employing a large air pump and can be operated by holding it in the hand.

It is preferred that the oral cleaning device be further provided with pulsation means which pulsates the cleaning liquid supplied to the ejection port. In this case, the cleaning liquid is ejected in a pulsatile manner from the ejection port. Therefore, it is possible to improve the cleaning effect with respect to periodontal pockets while reducing the amount of cleaning liquid to be used. The pulsation means may include providing a movable baffle plate or valve body or providing an impeller which is rotated by the cleaning liquid flowing through the cleaning liquid supply passage on the midway part of the cleaning liquid supply passage to pulsate the cleaning liquid, or providing means for continuously or intermittently supplying air to the cleaning liquid supply passage to pulsate the cleaning liquid by the air supplied to the cleaning liquid supply passage. When the cleaning liquid is pulsated by the air supplied to the cleaning liquid supply passage, the cleaning liquid and the air are alternately arranged inside the cleaning liquid supply passage to intermittently eject the cleaning liquid or fine air bubbles are mixed into the cleaning liquid inside the cleaning liquid supply passage to periodically change the flow rate of the cleaning liquid to thereby eject the cleaning liquid in a pulsatile manner from the ejection port. In this specification, "pulsatile ejection" includes both a case in which the cleaning liquid is intermittently ejected from the ejection port and a case in which the cleaning liquid is continuously ejected from the ejection port, but the flow rate thereof periodically changes. Further, "steady ejection" means that the cleaning liquid is continuously ejected from the ejection port without changing the flow rate thereof.

It is preferred that the pulsation means include providing an air introduction hole which is open on a midway part of the cleaning liquid supply passage and supplying part of the air supplied to the cleaning liquid tank from the air pump to the cleaning liquid supply passage through the air introduction hole to pulsate the cleaning liquid supplied to the ejection port. In this case, it is possible to eject the cleaning liquid in a pulsatile manner from the ejection port by alternately supplying the cleaning liquid and air or supplying the cleaning liquid mixed with fine air bubbles to the cleaning liquid supply passage on the downstream side with respect to the opening position of the air introduction hole with the simple configuration of providing the air introduction hole.

It is preferred that the following four relational expressions be satisfied, where A (m/sec) denotes the flow velocity of the cleaning liquid in the cleaning liquid supply passage, D1 (mm) denotes the opening diameter of the air introduction hole with respect to the cleaning liquid supply passage, and D2 (mm) denotes the flow passage diameter of the cleaning liquid supply passage near an opening of the air introduction hole.

$$3 \leq A \leq 40 \quad (1)$$

$$0.3 \leq D1 \leq 1.5 \quad (2)$$

$$1.5 \leq D2 \leq 5 \quad (3)$$

$$0.1 \leq D1/D2 \leq 0.5 \quad (4)$$

In this case, it is possible to reliably alternately supply the cleaning liquid and air to the cleaning liquid supply passage on the downstream side with respect to the opening position of the air introduction hole to thereby intermittently eject masses of cleaning liquid droplets from the ejection port. Thus, it is possible to prevent troubles such as supplying only the cleaning liquid to the ejection port, supplying only air, and ejecting the cleaning liquid in an atomized state. The above four relational expressions are satisfied when drinkable water such as tap water and mineral water with no oral cleaning agent added, the surface tension thereof being set to be substantially equal to or lower than that of pure water, is used as the cleaning liquid. Alternatively, a cleaning liquid obtained by adding, for example, an oral cleaning agent to drinkable water such as tap water and mineral water or an oral cleaning agent itself may also be used as the cleaning liquid. In this case, the cleaning liquid can be ejected in a pulsatile manner by appropriately setting the flow velocity A, the opening diameter D1, and the flow passage diameter D2 according to the viscosity and the surface tension of the cleaning liquid.

It is also preferred that an air introduction hole which is open on a midway part of the cleaning liquid supply passage be provided and part of the air supplied to the cleaning liquid tank from the air pump be supplied to the cleaning liquid supply passage through the air introduction hole to atomize the cleaning liquid supplied to the ejection port. In this case, it is possible to continuously eject the atomized cleaning liquid from the ejection port and clean the oral cavity with the atomized cleaning liquid. Further, it is possible to eject the atomized cleaning liquid with the simple configuration of providing the air introduction hole in the same manner as the case in which the cleaning liquid is ejected in a pulsatile manner by appropriately setting the flow velocity of the cleaning liquid in the cleaning liquid supply passage, the opening diameter of the air introduction hole with respect to the cleaning liquid supply passage, the flow passage diameter of the cleaning liquid supply passage near the opening of the air introduction hole, and the like. Further, the oral cleaning device configured in this manner can also serve as, other than cleaning of the oral cavity, an inhaler for throat or nose using an atomized agent by filling an inhalation agent for throat or nose in the cleaning liquid tank instead of the cleaning liquid.

It is preferred that the oral cleaning device be further provided with a narrowing portion which projects into the cleaning liquid supply passage to narrow the passage cross-sectional area, the narrowing portion being disposed at an opening position of the air introduction hole on the cleaning liquid supply passage. In this case, the passage area of the cleaning liquid supply passage is reduced in the narrowing portion to reduce the pressure of the cleaning liquid flowing through the cleaning liquid supply passage. Therefore, air is more smoothly introduced into the cleaning liquid supply passage through the air introduction hole.

It is preferred that the oral cleaning device be further provided with an air vent passage which opens the cleaning liquid tank to the atmosphere, a valve body which is capable of switching the air vent passage between an open state and a closed state, a power switch which operates supply of power to the air pump, and operation means which switches the valve body to a closed state in response to an ON operation of the power switch and to an open state in response to an OFF operation of the power switch. In this case, even when the internal pressure of the cleaning liquid tank increases, for example, in summer, air inside the cleaning liquid tank is discharged to the outside through the air vent passage. Therefore, it is possible to prevent a trouble such as leakage of the cleaning liquid from the ejection port caused by an increase in the internal pressure of the cleaning liquid tank. Further, since the air vent passage is switched between the open state and the closed state by the operation means in response to the operation of the power switch, it is possible to close the air vent passage to eject the cleaning liquid from the ejection port only when necessary, specifically, when the power switch is operated to be ON.

It is preferred that the oral cleaning device be further provided with a check valve which prevents leakage of the cleaning liquid through the air vent passage when the oral cleaning device falls over, the check valve being disposed on a midway part of the air vent passage. In this case, when the oral cleaning device falls over, the air vent passage is closed by the check valve. Therefore, it is possible to prevent the cleaning liquid inside the cleaning liquid tank from being discharged to the outside through the air vent passage.

It is preferred that the air pump include a rolling type air pump. The rolling type air pump is preferred because it is small and low cost as well as has a larger ejection flow rate.

It is preferred that an ejection port side part of the cleaning liquid supply passage be composed of a nozzle, and the outermost diameter of the nozzle be set at 3 mm or more and 8 mm or less in a region to be inserted into the oral cavity. When the outermost diameter of the nozzle is too small, the cleaning liquid supply passage becomes narrow, and a sufficient ejection pressure for the cleaning liquid cannot be obtained. On the other hand, when the outermost diameter of the nozzle is too large, it becomes difficult to operate the nozzle inside the oral cavity. Therefore, the outermost diameter of the nozzle is preferably set at 3 mm or more and 8 mm or less.

Advantageous Effects of Invention

In the oral cleaning device according to the present invention, air is supplied into the cleaning liquid tank by the electric air pump to pressurize the inside of the cleaning liquid tank, and the cleaning liquid inside the cleaning liquid tank is thereby supplied to the ejection port through the cleaning liquid supply passage by air pressure inside the cleaning liquid tank. Accordingly, the oral cavity can be cleaned by the cleaning liquid ejected from the ejection port. Further, since the cleaning liquid is ejected by the air pump in this manner, it is possible to reduce the load on driving means such as the motor in the air pump and ensure a sufficient ejection pressure for the cleaning liquid while employing a small and low-cost air pump with a low output, compared to the case in which a cleaning liquid is ejected by directly pressurizing the cleaning liquid by the piston pump as in the inventions described in Patent Documents 1 to 3. Therefore, the present invention is preferably applied to a handy type small oral cleaning device which has difficulty in employing a large air pump and can be operated by holding it in the hand.

BRIEF DESCRIPTION OF THE DRAWINGS

FIG. 1 is a perspective view of an oral cleaning device.
FIG. 2 is a plan view of the oral cleaning device.
FIG. 3 is a perspective view of the oral cleaning device with a cleaning liquid tank detached therefrom.
FIG. 4 is a perspective view of the oral cleaning device with a nozzle and an upper cover detached therefrom.
FIG. 5 is a cross-sectional view taken along line V-V of FIG. 2.
FIG. 6 is a cross-sectional view taken along line VI-VI of FIG. 2.
FIG. 7 is a cross-sectional view taken along line VII-VII of FIG. 2.
FIG. 8 is a cross-sectional view taken along line VIII-VIII of FIG. 5.
FIG. 9 is a longitudinal sectional view near an air supply hole.
FIG. 10(a) is an explanatory diagram of a check valve in an upright posture, FIG. 10(b) is an explanatory diagram of the check valve in a tilted posture, and FIG. 10(c) is an explanatory diagram of the check valve in an inverted posture.
FIG. 11 is an explanatory diagram of a testing device for evaluation of the cleaning performance with respect to periodontal pockets.
FIG. 12(a) is a photograph showing a peeled-off state of artificial plaque when a cleaning liquid is ejected in a pulsatile manner at a flow rate of 1.1 (L/min), and FIG. 12(b) is a peeled-off state of artificial plaque when the cleaning liquid is ejected in a steady manner at a flow rate of 1.1 (L/min).
FIG. 13(a) is a photograph showing a peeled-off state of artificial plaque when the cleaning liquid is ejected in a pulsatile manner at a flow rate of 2.1 (L/min), and FIG. 13(b) is a peeled-off state of artificial plaque when the cleaning liquid is ejected in a steady manner at a flow rate of 2.1 (L/min).
FIG. 14(a) is a photograph showing a peeled-off state of artificial plaque when the cleaning liquid is ejected in a pulsatile manner at a flow rate of 3.9 (L/min), and FIG. 14(b) is a peeled-off state of artificial plaque when the cleaning liquid is ejected in a steady manner at a flow rate of 3.9 (L/min).
FIG. 15 is a longitudinal sectional view of an oral cleaning device used for obtaining conditions for obtaining pulsatile ejection.
FIG. 16 is a graph showing the relationship between the ratio D1/D2 between the opening diameter D1 of an air introduction hole and the flow passage diameter of an ejection connection tube and the ejection pressure of an air pump.

DESCRIPTION OF EMBODIMENTS

Hereinbelow, an embodiment of the present invention will be described with reference to the drawings.

As illustrated in FIGS. 1 to 10(c), an oral cleaning device 1 is provided with an air-tightly closable cleaning liquid tank 2 which stores a cleaning liquid, a cleaning liquid supply passage 24 which has an ejection port 4a for ejecting the cleaning liquid into the oral cavity on one end and an introduction port 23a open inside the bottom part of the cleaning liquid tank 2 on the other end, and an electric air pump 44 which supplies air into the cleaning liquid tank 2 to pressurize the inside of the cleaning liquid tank 2. The cleaning liquid inside the cleaning liquid tank 2 is supplied to the ejection port 4a through the cleaning liquid supply passage 24 by air pressure inside the cleaning liquid tank 2.

More specifically, the oral cleaning device 1 is a handy type oral cleaning device which can be operated by holding it in the hand. The oral cleaning device 1 is provided with a cleaning device body 3, and the cleaning liquid tank 2 and a nozzle 4 both of which are detachably attached to the cleaning device body 3. The cleaning device body 3 is provided with a vertically elongated casing 10, a support frame 11 which is internally fitted to the casing 10, a charging induction coil 41 an a circuit board 42 both of which are attached to the support frame 11 and assembled inside the casing 10 together with the support frame 11, a secondary battery 43, an air pump 44, an air supply tube 49 which supplies air from the air pump 44 to the cleaning liquid tank 2, an air vent tube 51 which opens the cleaning liquid tank 2 to the atmosphere inside the casing 10, two check valves 60, 61 which are disposed on the midway part of the air vent tube 51, a valve body 53 which is capable of switching the air vent tube 51 between an open state and a closed state, a power switch 45 which operates the supply of power to the air pump 44, and an operation button 52 which switches the valve body 53 to a closed state in response to an ON operation of the power switch 45 and switches the valve body 53 to an open state in response to an OFF operation of the power switch 45.

(Cleaning Liquid)

Drinkable water such as tap water and mineral water whose surface tension is substantially equal to that of pure water, the drinkable water with an oral cleaning agent added, or an oral cleaning agent itself may be preferably employed as the cleaning liquid. For example, a mouthwash, a liquid dentifrice, or a gargle may be employed as the agent.

(Casing)

The casing 10 of the cleaning device body 3 is provided with a lower case 12 and an upper case 13 which is attached to the lower case 12 to cover the upper side of the lower case 12. The lower case 12 includes a bottomed main body 14 which is vertically elongated and a support wall 15 which projects to the lateral side from the upper end of the main body 14.

(Nozzle)

The nozzle 4 is composed of an elongated hollow pipe member. The ejection port 4a is formed on the tip of the nozzle 4. A tip part of the nozzle 4 is bent by approximately 20° so as to easily spray the cleaning liquid to interdental spaces. A flange 4b for attaching/detaching operation is formed near the lower end of the nozzle 4. A tubular attachment portion 4c is formed on the lower end of the nozzle 4, and a seal ring 5 is externally fitted to the attachment portion 4c. The nozzle 4 is detachably attached to the upper case 13 by internally and liquid-tightly fitting the attachment portion 4c on the lower end thereof to a nozzle attaching recess 16 which is formed on the upper case 13. When the outermost diameter of the nozzle 4 above the flange 4b is too small, the cleaning liquid supply passage 24 becomes narrow, and a sufficient ejection pressure for the cleaning liquid cannot be obtained. On the other hand, when the outermost diameter of the nozzle 4 above the flange 4b is too large, it becomes difficult to operate the nozzle 4 inside the oral cavity. Therefore, the outermost diameter of the nozzle 4 above the flange 4b is preferably set at 3 mm or more and 8 mm or less.

(Cleaning Liquid Supply Passage)

An ejection connection tube 20 which projects both upward and downward is integrally formed with a substantially central part of the support wall 15 of the lower case 12. A connection tubular portion 21 which projects downward is formed at a position corresponding to the nozzle attaching recess 16 of the upper case 13. Assembling the upper case 13 to the lower case 12 allows the upper end of the ejection connection tube 20 to be internally and liquid-tightly fitted to the connection tubular portion 21 with a seal ring 22 interposed therebetween. A supply pipe 23 is liquid-tightly connected to the lower end of the ejection connection tube 20. The introduction port 23a which is open inside the lower end part of the cleaning liquid tank 2 is formed on the lower end of the supply pipe 23. The supply pipe 23, the ejection connection tube 20, and the nozzle 4 together form the cleaning liquid supply passage 24 which allows the ejection port 4a on the tip of the nozzle 4 and the introduction port 23a on the lower end of the supply pipe 23 to communicate with each other.

(Cleaning Liquid Tank)

The cleaning liquid tank 2 is an elongated bottomed member which has a semicylindrical cross section. The cleaning liquid tank 2 is detachably attached to the lateral side of the main body 14 of the lower case 12 at a position under the support wall 15 of the lower case 12. The outer face of the cleaning liquid tank 2 is smoothly connected to the lower case 12 and the support wall 15 when the cleaning liquid tank 2 is assembled to the casing 10 so as to have a square cross-sectional shape whose four corners are rounded.

An elliptic tubular mouth portion 30 which projects upward is formed on the upper face of the cleaning liquid tank 2. A seal ring 31 is externally fitted to a midway part in the height direction of the mouth portion 30. A fitting recess 32 is formed on the lower face of the support wall 15 of the lower case 12, and the mouth portion 30 can be internally and air-tightly fitted to the fitting recess 32.

A pair of vertically elongated fitting grooves 33 is formed on the lower half part of a side wall 14a of the main body 14 of the lower case 12, the side wall 14a facing the cleaning liquid tank 2. The fitting grooves 33 are parallel to each other with a distance therebetween. A pair of vertically elongated projections 34 is formed on the lower half part of a side wall 2a of the cleaning liquid tank 2, the side wall 2a facing the main body 14 of the lower case 12. Each of the projections 34 has an L-shaped cross section. The projections 34 are formed with a distance therebetween. A locking recess 35 is formed on the lower end of the side wall 14a of the lower case 12. A locking projection 36 which can be engaged with the locking recess 35 is formed on the lower end of the side wall 2a of the cleaning liquid tank 2.

When the cleaning liquid tank 2 is attached to the casing 10, the upper part of the side wall 2a of the cleaning liquid tank 2 is brought to overlap the lower part of the side wall 14a of the main body 14 to fit the projections 34 with the respective fitting grooves 33, and the cleaning liquid tank 2 is then relatively moved upward to thereby allow the mouth portion 30 to be internally and liquid-tightly fitted to the fitting recess 32 of the support wall 15. In this state, the locking projection 36 is engaged with the locking recess 35, so that the cleaning liquid tank 2 is assembled to the casing 10 in a manner to prevent lateral and vertical movement of the cleaning liquid tank 2. On the other hand, when the cleaning liquid tank 2 is detached from the casing 10, the cleaning liquid tank 2 is forcibly moved downward relative to the casing 10 with a little force to release the engagement between the locking projection 36 and the locking recess 35. Then, the cleaning liquid tank 2 is further moved downward relative to the casing 10, so that the cleaning liquid tank 2 can be detached from the casing 10.

An injection port 37 which projects outward is formed on the lower part of the cleaning liquid tank 2. A lid 38 is liquid-tightly and detachably attached to the injection port 37 with a seal ring 39 interposed therebetween. Accordingly, the cleaning liquid can be filled through the injection port 37 without detaching the cleaning liquid tank 2 from the casing 10. However, an attachment structure other than the above may be employed as the attachment structure of the cleaning liquid tank 2 to the casing 10. The injection port 37 and the lid 38 may be omitted, and the cleaning liquid may be filled into the cleaning liquid tank 2 through the mouth portion 30 with the cleaning liquid tank 2 detached from the casing 10.

Further, it is also preferred that an accumulator which temporarily stores air from the air pump 44 be formed, for example, on the upper part of the cleaning liquid tank 2 to reduce fluctuation of the ejection pressure for the cleaning liquid.

(Power Supply Device)

A power supply device 40 of the oral cleaning device 1 is provided with the charging induction coil 41, the circuit board 42 which includes a conversion circuit for converting an electromotive force of the induction coil 41 into a DC power supply, the secondary battery 43 such as a nickel-hydrogen secondary battery and a lithium ion secondary battery, and the power switch 45 which switches the supply of power to the air pump 44 between an ON state and an OFF state.

The induction coil 41 is disposed inside the lower end part of the lower case 12. The oral cleaning device 1 is vertically placed on a charger (not illustrated) to thereby cause the induction coil 41 to generate an electromotive force by electromagnetic induction so that the secondary battery 43 can be charged. In the present embodiment, contactless charging is employed in order to improve the liquid-tightness of the oral cleaning device 1. Alternatively, contact charging may be employed, the secondary battery 43 may be taken out to be charged outside the device, a primary battery may be used instead of the secondary battery 43 to drive the air pump 44, or an AC power supply may directly drive the air pump 44 through an AC/DC adapter.

(Air Pump)

The air pump 44 is disposed inside the upper half part of the main body 14 of the lower case 12 at a position above the circuit board 42 and the secondary battery 43. The air pump 44 is provided with a pump body 46 and a motor 47 which drives the pump body 46. The air pump 44 is composed of a known rolling type air pump. An ejection tube 46a is disposed on the upper part of the pump body 46. An introduction connection tube 48 which is open inside the upper part of the cleaning liquid tank 2 is disposed in a standing manner on the support wall 15 of the lower case 12 beside the ejection connection tube 20. The ejection tube 46a and the introduction connection tube 48 are connected to each other through the air supply tube 49 which is composed of a flexible pipe member. Air ejected from the air pump 44 is supplied into the upper part of the cleaning liquid tank 2 through the ejection tube 46a, the air supply tube 49, and the introduction connection tube 48. A known air pump other than a rolling type air pump may be employed as the air pump 44.

(Air Vent Passage, Operation Means)

A discharge connection tube 50 is disposed in a standing manner on the support wall 15 of the lower case 12 beside the ejection connection tube 20. The air vent tube 51 is connected to the discharge connection tube 50. The air vent tube 51 extends through the inside of the upper case 13 up to a position facing a side wall of the upper case 13, the side wall being located opposite to the cleaning liquid tank 2. An opening 51a is formed on an end of the air vent tube 51, the end being located opposite to the discharge connection tube 50. The operation button 52 made of an elastic member is disposed on a side wall of the upper case 13, the side wall being located on the same side as the air pump 44, in a manner to face the opening 51a of the air vent tube 51. The valve body 53 which is capable of opening and closing the opening 51a of the air vent tube 51 is disposed on the end of the air vent tube 51 in a manner to face the operation button 52. The valve body 53 is normally held in an open state by a coil spring as biasing means 54 to open the cleaning liquid tank 2 to the atmosphere through an air vent passage 55 inside the discharge connection tube 50 and the air vent tube 51. Depressing the operation button 52 with the finger to press the valve body 53 toward the air vent tube 51 by the operation button 52 against the biasing force of the biasing means 54 enables the opening 51a of the air vent tube 51 to be air-tightly closed by the valve body 53. Operation means includes the operation button 52, the biasing means 54, and the like.

The power switch 45 which operates the supply of power to the air pump 44 is disposed under the valve body 53. A switch portion of the power switch 45 extends upward and abuts against the operation button 52. When the operation button 52 is depressed, the power switch 45 is turned ON and the opening 51a of the air vent tube 51 is closed by the valve body 53. Accordingly, the air pump 44 is driven to supply air from the air pump 44 into the upper part of the cleaning liquid tank 2, which increases the internal pressure of the cleaning liquid tank 2. As a result, the cleaning liquid inside the cleaning liquid tank 2 is ejected from the ejection port 4a of the nozzle 4 through the cleaning liquid supply passage 24. On the other hand, when the finger is released from the operation button 52, the operation button 52 is elastically returned to turn OFF the power switch 45 and allow the valve body 53 to move back to open the opening 51a of the air vent tube 51. Accordingly, the supply of air from the air pump 44 into the cleaning liquid tank 2 is stopped and the cleaning liquid tank 2 is opened to the atmosphere through the air vent passage 55. As a result, it is possible to stop the ejection of the cleaning liquid with good draining without leakage of the cleaning liquid from the nozzle 4.

(Check Valve)

The first check valve 60 and the second check valve 61 are disposed on the midway part of the air vent tube 51 in order to prevent the cleaning liquid inside the cleaning liquid tank 2 from being discharged into the casing 10 through the opening 51a of the air vent tube 51, for example, when the oral cleaning device 1 is largely tilted or falls over.

The first check valve 60 will be described. As illustrated in FIGS. 7 and 10(a) to 10(c), a first passage 62 is formed on the air vent tube 51 at a position near a part connected to the discharge connection tube 50. The first passage 62 is aligned with the up-down direction when the oral cleaning device 1 is held in an upright posture. A steel ball 63 is placed inside the first passage 62 movably by a certain distance. When the posture of the oral cleaning device 1 is within a range from an upright posture illustrated in FIG. 10(a) to a horizontal posture, the steel ball 63 is located on the upstream side (lower side) of the first passage 62 to open the first passage 62. On the other hand, when the oral cleaning device 1 is further tilted from the horizontal posture to an inverted posture illustrated in FIG. 10(b), the steel ball 63 moves to the downstream side (upper side) of the first passage 62 to close the first passage 62.

The second check valve 61 will be described. As illustrated in FIGS. 7 and 10(a) to 10(c), a second passage 64 is formed on the midway part of the air vent tube 51. The second passage 64 is tilted by a tilt angle $\theta$ of approximately 30° with respect to the horizontal direction based on the oral cleaning device 1 in the upright posture within a plane including a movement locus of the nozzle 4 during cleaning of interdental spaces. A steel ball 65 is placed inside the second passage 64 movably by a certain distance. When the tilt angle from the upright posture of the oral cleaning device 1 is within the range of 30°, the steel ball 65 is located on the upstream side of the second passage 64 to open the second passage 64 as illustrated in FIG. 10(a). On the other hand, when the tilt angle from the upright posture is 30° or more, the steel ball 65 moves to the downstream side of the second passage 64 to close the second passage 64 as illustrated in FIG. 10(c).

That is, when the tilt angle from the upright posture of the oral cleaning device 1 is within the range of 30°, the first passage 62 and the second passage 64 are opened to open the air vent passage 55 to the atmosphere. On the other hand, when the tilt angle from the upright posture of the oral cleaning device 1 is 30° or more, the second check valve 61 is closed to prevent the cleaning liquid inside the cleaning liquid tank 2 from leaking into the casing 10 through the air vent passage 55 as illustrated in FIG. 10(c). Further, the oral cleaning device 1 may be caused to fall over. In this case, when the posture of the oral cleaning device 1 is tilted toward the inverted posture over the horizontal posture, the first check valve 60 is closed to prevent the cleaning liquid inside the cleaning liquid tank 2 from leaking into the casing 10 through the air vent passage 55 as illustrated in FIG. 10(b). Although the discharge connection tube 50, the air vent tube 51, the valve body 53, the biasing means 54, and the check valves 60 and 61 are preferably provided in order to prevent the leakage of the cleaning liquid from the nozzle 4, these members may also be omitted.

The oral cleaning device 1 is provided with pulsation means 70 which pulsates the cleaning liquid ejected from the ejection port 4a of the nozzle 4 in order to improve the cleaning effect inside the oral cavity. Although the pulsation means 70 is preferably provided in order to improve the cleaning effect, the oral cleaning device 1 which is not provided with the pulsation means 70 also falls within the scope of the present invention. In this specification, "pulsatile ejection" includes both a case in which the cleaning liquid is intermittently ejected from the ejection port 4a of the nozzle 4 and a case in which the cleaning liquid is continuously ejected from the ejection port 4a of the nozzle 4, but the flow rate thereof periodically changes. Further, "steady ejection" means that the cleaning liquid is continuously ejected from the ejection port 4a of the nozzle 4 without changing the flow rate thereof.

(Pulsation Means)

As illustrated in FIGS. 5 and 9, an air introduction hole 71 which is open inside the cleaning liquid tank 2 is formed on the lower end part of the ejection connection tube 20. A narrowing portion 72 which projects inward to reduce the passage area of the ejection connection tube 20 is formed on the upstream side (lower side) of the opening position of the air introduction hole 71. Alternatively, it is also preferred that the air introduction hole 71 be open on the top of the narrowing portion 72. Further, the narrowing portion 72 may be omitted by appropriately setting the opening diameter of the air introduction hole 71 and the flow passage diameter of the ejection connection tube 20.

In the pulsation means 70, air inside the cleaning liquid tank 2 is supplied into the cleaning liquid supply passage 24 through the air introduction hole 71. Accordingly, the cleaning liquid and the air are alternately supplied or the cleaning liquid mixed with fine air bubbles is supplied into the cleaning liquid supply passage 24 on the downstream side with respect to the opening position of the air introduction hole 71, so that the cleaning liquid is ejected in a pulsatile manner from the ejection port 4a of the nozzle 4.

In order to achieve the pulsatile ejection of the cleaning liquid inside the cleaning liquid tank 2 in this manner, the following four relational expressions are satisfied, where A (m/sec) denotes the flow velocity of the cleaning liquid in the cleaning liquid supply passage 24, D1 (mm) denotes the opening diameter of the air introduction hole 71 with respect to the cleaning liquid supply passage 24, and D2 (mm) denotes the flow passage diameter of the cleaning liquid supply passage 24 near the opening of the air introduction hole 71 excepting the narrowing portion 72. Such a configuration makes it possible to set the ejection pressure for the cleaning liquid ejected from the nozzle 4 at 1 to 10 kgf/cm² which enables plaque to be efficiently removed and set the number of times of ejection per one minute at 1000 to 2000 even in the handy type oral cleaning device.

$$3 \le A \le 40 \tag{1}$$

$$0.3 \le D1 \le 1.5 \tag{2}$$

$$1.5 \le D2 \le 5 \tag{3}$$

$$0.1 \le D1/D2 \le 0.5 \tag{4}$$

When the flow velocity A of the cleaning liquid is low, water inside the cleaning liquid tank 2 cannot be pushed out. On the other hand, when the flow velocity A is high, water inside the cleaning liquid tank 2 is atomized. Therefore, the flow velocity A is set at 3 m/sec or more and 40 m/sec or less.

When the opening diameter D1 of the air introduction hole 71 is too small, introduction of air into the cleaning liquid supply passage 24 becomes difficult and the cleaning liquid is ejected in a steady manner. On the other hand, when the opening diameter D1 is too large, the cleaning liquid is not supplied to the nozzle 4 and only air is ejected from the nozzle 4. Therefore, the opening diameter D1 is set at 0.3 mm or more and 1.5 mm or less.

When the flow passage diameter D2 of the cleaning liquid supply passage 24 is small, the pressure loss inside the cleaning liquid supply passage 24 increases and an effective ejection pressure thus cannot be obtained. On the other hand, when the flow passage diameter D2 is too large, the cleaning liquid inside the cleaning liquid tank 2 cannot be pushed out. Therefore, the flow passage diameter D2 is set at 1.5 mm or more and 5 mm or less.

When the ratio D1/D2 between the opening diameter D1 of the air introduction hole 71 and the flow passage diameter D2 of the cleaning liquid supply passage 24 is too small, the pulsatile ejection cannot be obtained. On the other hand, when the ratio D1/D2 is too large, the cleaning liquid is not supplied to the nozzle 4 and only air is ejected from the nozzle 4. Therefore, the ratio D1/D2 is set at 0.1 or more and 0.5 or less.

The above four relational expressions are satisfied when drinkable water such as tap water and mineral water with no oral cleaning agent added, the surface tension thereof at 20° C. being set within substantially the same range as that of pure water, specifically, 72.75 mN/m or lower, preferably within the range of 72.75±30 mN/m, more preferably within the range of 72.75±25 mN/m, and further more preferably within the range of 72.75±20 mN/m, is used as the cleaning liquid. Alternatively, a cleaning liquid obtained by adding, for example, an oral cleaning agent to drinkable water such as tap water and mineral water may also be used as the cleaning liquid. In this case, the cleaning liquid can be ejected in a pulsatile manner by appropriately setting the flow velocity A, the opening diameter D1, and the flow passage diameter D2 according to the viscosity and the surface tension of the cleaning liquid. That is, values of the flow velocity A (m/sec) of the cleaning liquid in the cleaning liquid supply passage 24, the opening diameter D1 (mm) of the air introduction hole 71, and the flow passage diameter D2 (mm) of the cleaning liquid supply passage 24 may be appropriately set according to the performance of the air pump 44 and the physical properties such as the surface tension and the viscosity of the cleaning liquid as long as the cleaning liquid and air are alternately supplied to the nozzle 4 to eject the cleaning liquid in a pulsatile manner from the nozzle 4.

The pulsation means 70 may be configured in such a manner that air from one cylinder of a rolling pump is directly connected to the air introduction hole 71 to supply the air to the cleaning liquid supply passage 24 or an additional air pump is provided to supply air to the cleaning liquid supply passage 24. Further, the air introduction hole 71 may be omitted, and a movable baffle plate, an impeller which is rotated by the cleaning liquid, or an on-off valve may be disposed on the midway part of the cleaning liquid supply passage 24 to eject the cleaning liquid in a pulsatile manner.

(Operation of Oral Cleaning Device)

When the oral cleaning device 1 cleans the oral cavity, the cleaning liquid, for example, water or water with an agent added is filled into the cleaning liquid tank 2. Then, the oral cleaning device 1 is held in the hand, and the nozzle 4 is inserted into the oral cavity in such a manner that the tip of the nozzle 4 is arranged at a desired position in the oral cavity. Then, the operation button 52 is depressed to eject the cleaning liquid in a pulsatile manner from the nozzle 4 to thereby clean interdental spaces, periodontal pockets, and the like. More specifically, when the operation button 52 is depressed, the power switch 45 is turned ON and the opening 51a of the air vent tube 51 is closed by the valve body 53. Accordingly, the air pump 44 is driven to supply air from the air pump 44 into the upper part of the cleaning liquid tank 2, which increase the internal pressure of the cleaning liquid tank 2. As a result, the cleaning liquid inside the cleaning liquid tank 2 is ejected from the ejection port 4a of the nozzle 4 through the cleaning liquid supply passage 24. At this point, part of the air supplied to the cleaning liquid tank 2 from the air pump 44 is introduced into the cleaning liquid supply passage 24 through the air introduction hole 71. Accordingly, the cleaning liquid and the air are alternately supplied or the cleaning liquid mixed with fine air bubbles is supplied into the cleaning liquid supply passage 24 on the downstream side with respect to the opening position of the air introduction hole 71, so that the cleaning liquid is ejected in a pulsatile manner from the ejection port 4a of the nozzle 4. On the other hand, when the finger is released from the operation button 52, the operation button 52 is elastically returned to turn OFF the power switch 45 and allow the valve body 53 to move back by the biasing force of the biasing means 54 to open the opening 51a of the air vent tube 51. Accordingly, the supply of air from the air pump 44 into the cleaning liquid tank 2 is stopped and the cleaning liquid tank 2 is opened to the atmosphere through the air vent passage 55. As a result, it is possible to stop the ejection of the cleaning liquid with good draining without leakage of the cleaning liquid from the nozzle 4.

In the oral cleaning device 1, the cleaning liquid is ejected by the air pump 44 in this manner. Thus, it is possible to reduce the load on the motor 47 of the air pump 44 and ensure a sufficient ejection pressure for the cleaning liquid while employing a small and low-cost air pump with a low output as the air pump 44, compared to a case in which the cleaning liquid is ejected by directly pressurizing the cleaning liquid by a piston pump as in the inventions described in Patent Documents 1 to 3. In addition, it is possible to improve the cleaning effect with respect to periodontal pockets by ejecting the cleaning liquid in a pulsatile manner from the nozzle 4 with a simple configuration of providing the air introduction hole 71, compared to a case in which the cleaning liquid is ejected in a steady manner.

Although, in the present embodiment, the cleaning liquid is ejected in a pulsatile manner from the ejection port 4a of the nozzle 4 in the oral cleaning device 1, the cleaning liquid may be ejected in an atomized state. In this case, the cleaning liquid is atomized by allowing the following four relational expression to be satisfied, where A (m/sec) denotes the flow velocity of the cleaning liquid in the cleaning liquid supply passage 24, D1 (mm) denotes the opening diameter of the air introduction hole 71 with respect to the cleaning liquid supply passage 24, and D2 (mm) denotes the flow passage diameter of the cleaning liquid supply passage 24 near the opening of the air introduction hole 71 excepting the narrowing portion 72. The oral cleaning device 1 configured in this manner can also serve as, other than cleaning of the oral cavity, an inhaler for throat or nose using an atomized agent by filling an inhalation agent for throat or nose in the cleaning liquid tank 2 instead of the cleaning liquid. The following four relational expressions are satisfied when drinkable water such as tap water and mineral water with no oral cleaning agent added, the surface tension thereof at 20° C. being set within substantially the same range as that of pure water, specifically, 72.75 mN/m or lower, preferably within the range of 72.75±30 mN/m, more preferably within the range of 72.75±25 mN/m, and further more preferably within the range of 72.75±20 mN/m, is used as the cleaning liquid.

$$5 \leq A \leq 50 \tag{1}$$

$$0.3 \leq D1 \leq 2 \tag{2}$$

$$1.5 \leq D2 \leq 5 \tag{3}$$

$$0.2 \leq D1/D2 \leq 0.7 \tag{4}$$

In the present embodiment, there has been described the case in which the present invention is applied to the handy type oral cleaning device 1 which can be operated by holding it in the hand. However, the present invention may also be applied to a stationary type oral cleaning device.

Next, an evaluation test for the cleaning performance with respect to periodontal pockets when the cleaning liquid is ejected in a pulsatile manner and in a steady manner will be described.

As illustrated in FIGS. 11(a) and 11(b), a testing device 80 configured in the following manner was prepared. A plate-like silicone impression material 82 which corresponds to gums is laminated on the lower half part of an acrylic plate 81. An abrasive film 83 to which artificial plaque is adhered is interposed between the acrylic plate 81 and the silicone impression material 82 in such a manner that the artificial plaque faces the silicone impression material 82 and the upper part thereof is arranged above the silicone impression material 82.

Then, as illustrated in FIG. 11(b), tap water as the cleaning liquid was jetted at an angle of 45° with respect to the horizontal plane for 10 seconds from the nozzle 4 to the boundary between the abrasive film 83 and the silicone impression material 82. Then, a peeled-off state of the artificial plaque adhered to the abrasive film 83 was photographed. This operation was performed while changing the flow rate of water ejected from the nozzle 4 to three patterns, specifically, 1.1 (L/min), 2.1 (L/min), and 3.9 (L/min) for each of the cases in which water was ejected in a pulsatile manner and in a steady manner from the nozzle 4. FIGS. 12(*a*) to 14(*b*) show a result of the test. In each of the photographs, a black part indicates a part in which the artificial plaque remains and a white part indicates a part in which the artificial plaque has been removed.

The result shows that the pulsatile ejection of water makes it possible to remove the artificial plaque located at a deeper position from the boundary B between the abrasive film 83 and the silicone impression material 82 than the steady ejection regardless of the flow rate of the ejected water.

(Condition Setting Test)

Next, a test performed for obtaining conditions for ejecting the cleaning liquid in a pulsatile manner from the nozzle 4 by forming the air introduction hole 71 will be described.

First, a cleaning liquid ejection device 90 used as a testing device will be described.

As illustrated in FIG. 15, the cleaning liquid ejection device 90 is provided with a bottomed tubular cleaning liquid tank 91 which is capable of storing a cleaning liquid, a lid 92 which is capable of air-tightly closing an upper end opening of the cleaning liquid tank 91, and a nozzle 93 which is detachably attached to the lid 92.

An ejection connection tube 92*a* which communicates with the nozzle 93 is formed on the lid 92 in a manner to project into the cleaning liquid tank 91. A supply pipe 94 is liquid-tightly connected to the lower end of the ejection connection tube 92*a*. The lower end of the supply pipe 94 is open inside the lower end part of the cleaning liquid tank 91. Inside the cleaning liquid tank 91, an air introduction hole 95 is formed near the lower end of the ejection connection tube 92*a*, and a narrowing portion 96 is formed in a projecting manner on the ejection connection tube 92*a* on the upstream side with respect to the air introduction hole 95. The maximum height of the narrowing portion 96 from the inner face of the ejection connection tube 92*a* is set at 0.7 mm in order to reduce the pressure loss. The height H between the lower end of the cleaning liquid tank 91 and the upper end face of the lid 92 is set at 160 mm in view of the size of the product device.

An air pump 97 (RFP32B03R manufactured by OKEN-SEIKO Co, Ltd.) is connected to the upper part of the cleaning liquid tank 91. Air is supplied into the cleaning liquid tank 91 from the air pump 97 to pressurize the inside of the cleaning liquid tank 91 so that the cleaning liquid can be ejected through the supply pipe 94, the ejection connection tube 92*a*, and the nozzle 93.

(Testing Method)

Tap water as the cleaning liquid was filled into the cleaning liquid tank 91 of the cleaning liquid ejection device 90. The voltage applied to the air pump 97 was adjusted to change the flow rate (L/min) of the air pump 97 to 1.1, 2.1, 3.9, 4.2, 4.5, 4.7, 7.6, and 9.4. For each flow rate, an ejection state of the water from the nozzle 93 was visually checked, and the flow velocity (m/sec) of the cleaning liquid in the ejection connection tube 92*a* was calculated when twenty kinds of lids 92 having different ratios D1/D2 obtained by setting the opening diameter D1 of the air introduction hole 95 and the flow passage diameter D2 of the ejection connection tube 92*a* as shown in Table 1 were used. Table 2 shows a result of the test. Further, FIG. 16 is a graph showing the relationship between the ratio D1/D2 and the ejection pressure of the air pump 97.

Each term (expression) in Table 2 indicates the following state.

(1) "No ejection" indicates a case in which no water, but only air was ejected from the nozzle 93.

(2) "Not ejected to the end" indicates a case in which steady ejection was performed until the middle, but only air is ejected from the nozzle 93 from the middle.

(3) "Steady ejection" indicates a case in which steady ejection was performed from the beginning to the end.

(4) "Pulsatile ejection only at the beginning" indicates a case in which pulsatile ejection was performed at the beginning, but switched to steady ejection from the middle.

(5) "Pulsatile ejection from the middle" indicates a case in which steady ejection was performed at the beginning, but switched to pulsatile ejection from the middle.

(6) "Pulsatile ejection only at the end" indicates a case in which steady ejection was performed at the beginning, but switched to pulsatile ejection at the end.

(7) A symbol "○" indicates that water was ejected in a pulsatile manner, and a value in parentheses behind the symbol "○" indicates the ejection pressure (kgf/cm$^2$) of the air pump 97 at that time.

(8) "Atomized" indicates that water in an atomized state was ejected from the nozzle 93. A value in parentheses indicates the ejection pressure (kgf/cm$^2$) of the air pump 97 at that time.

TABLE 1

| | | Opening diameter D1 (mm) of air introduction hole | | | |
|---|---|---|---|---|---|
| | | 0.5 | 1 | 1.5 | 2 |
| Flow passage diameter D2 (mm) of ejection connection tube | 2 | 0.25 | 0.5 | 0.75 | 1 |
| | 3 | 0.17 | 0.33 | 0.5 | 0.67 |
| | 4 | 0.13 | 0.25 | 0.38 | 0.5 |
| | 5 | 0.1 | 0.2 | 0.3 | 0.4 |
| | 6 | 0.04 | 0.08 | 0.13 | 0.17 |

TABLE 2

| | | Opening diameter D1 (mm) of air introduction hole | | | | Flow velocity |
|---|---|---|---|---|---|---|
| | | 0.5 | 1 | 1.5 | 2 | (m/sec) |
| Flow rate (L/min) 1.1 | | | | | | |
| Flow passage diameter D2 (mm) | 2 | No ejection | No ejection | No ejection | No ejection | 5.84 |
| | 3 | No ejection | No ejection | No ejection | No ejection | 2.59 |
| | 4 | Steady ejection | No ejection | No ejection | No ejection | 1.46 |
| | 5 | Steady ejection | No ejection | No ejection | No ejection | 0.94 |
| | 6 | Steady ejection | No ejection | No ejection | No ejection | 0.65 |

TABLE 2-continued

| | | Opening diameter D1 (mm) of air introduction hole | | | | Flow velocity |
|---|---|---|---|---|---|---|
| | | 0.5 | 1 | 1.5 | 2 | (m/sec) |
| Flow rate (L/min) 2.1 | | | | | | |
| Flow passage diameter D2 (mm) | 2 | ○ (1.3) | Not ejected to the end | Not ejected to the end | No ejection | 11.14 |
| | 3 | ○ (1.54) | Pulsatile ejection from the middle | Not ejected to the end | No ejection | 4.95 |
| | 4 | Pulsatile ejection only at the end | Not ejected to the end | Not ejected to the end | No ejection | 2.79 |
| | 5 | Steady ejection | Not ejected to the end | Not ejected to the end | No ejection | 1.78 |
| | 6 | Steady ejection | Not ejected to the end | Not ejected to the end | Not ejected to the end | 1.24 |
| Flow rate (L/min) 3.9 | | | | | | |
| Flow passage diameter D2 (mm) | 2 | ○ (2.56) | Not ejected to the end | Not ejected to the end | No ejection | 20.69 |
| | 3 | ○ (3.34) | Atomized (2.96) | Atomized (2.5) | No ejection | 9.2 |
| | 4 | ○ (3.48) | Atomized (3.12) | Atomized (2.58) | No ejection | 5.17 |
| | 5 | Pulsatile ejection only at the end | Pulsatile ejection only at the end | Not ejected to the end | Not ejected to the end | 3.31 |
| | 6 | Steady ejection | Pulsatile ejection only at the end | Not ejected to the end | Not ejected to the end | 2.3 |
| Flow rate (L/min) 4.2 | | | | | | |
| Flow passage diameter D2 (mm) | 2 | ○ (2.12) | Atomized (2.48) | Not ejected to the end | No ejection | 22.28 |
| | 3 | ○ (3) | ○ (2.56) | Atomized (2.28) | No ejection | 9.9 |
| | 4 | ○ (3.12) | ○ (2.78) | Not ejected to the end | Not ejected to the end | 5.57 |
| | 5 | Steady ejection | Pulsatile ejection from the middle | Not ejected to the end | Not ejected to the end | 3.57 |
| | 6 | Steady ejection | Pulsatile ejection from the middle | Not ejected to the end | Not ejected to the end | 2.48 |
| Flow rate (L/min) 4.5 | | | | | | |
| Flow passage diameter D2 (mm) | 2 | ○ (3.76) | Atomized (3.14) | Not ejected to the end | No ejection | 23.87 |
| | 3 | ○ (3.76) | ○ (3.72) | Not ejected to the end | No ejection | 10.61 |
| | 4 | ○ (3.84) | ○ (3.72) | Not ejected to the end | Not ejected to the end | 5.97 |
| | 5 | Pulsatile ejection only at the end | Pulsatile ejection from the middle | Pulsatile ejection from the middle | Not ejected to the end | 3.82 |
| | 6 | Steady ejection | Pulsatile ejection from the middle | Pulsatile ejection from the middle | Not ejected to the end | 2.65 |
| Flow rate (L/min) 4.7 | | | | | | |
| Flow passage diameter D2 (mm) | 2 | ○ (2.84) | Atomized (1.96) | Not ejected to the end | No ejection | 24.93 |
| | 3 | ○ (3.58) | ○ (3.28) | Not ejected to the end | No ejection | 11.08 |
| | 4 | ○ (3.76) | ○ (3.34) | Not ejected to the end | Not ejected to the end | 6.23 |
| | 5 | Pulsatile ejection only at the end | Pulsatile ejection from the middle | Not ejected to the end | Not ejected to the end | 3.99 |
| | 6 | Steady ejection | Pulsatile ejection from the middle | Pulsatile ejection from the middle | Not ejected to the end | 2.77 |
| Flow rate (L/min) 7.6 | | | | | | |
| Flow passage diameter D2 (mm) | 2 | Atomized (3.38) | ○ (3.58) | Not ejected to the end | No ejection | 40.32 |
| | 3 | Atomized (3.98) | ○ (3.64) | Atomized (3.32) | Not ejected to the end | 17.92 |
| | 4 | ○ (3.86) | ○ (3.92) | Atomized (3.1) | Not ejected to the end | 10.08 |
| | 5 | Pulsatile ejection only at the end | Pulsatile ejection from the middle | Atomized (3.76) | Not ejected to the end | 6.45 |
| | 6 | Steady ejection | Pulsatile ejection from the middle | Not ejected to the end | Not ejected to the end | 4.48 |
| Flow rate (L/min) 9.4 | | | | | | |
| Flow passage diameter D2 (mm) | 2 | Atomized (2.88) | Atomized (3.02) | Not ejected to the end | Not ejected to the end | 49.89 |
| | 3 | ○ (3.46) | Atomized (3.42) | Atomized (3.72) | Not ejected to the end | 22.16 |
| | 4 | ○ (3.6) | Atomized (3.7) | Atomized (3.5) | Not ejected to the end | 12.47 |
| | 5 | Pulsatile ejection only at the end | Pulsatile ejection from the middle | Atomized (3.56) | Not ejected to the end | 7.98 |
| | 6 | Steady ejection | Pulsatile ejection from the middle | Not ejected to the end | Not ejected to the end | 5.54 |

Table 2 and FIG. 16 show that it is possible to alternately feed the cleaning liquid and air to the downstream side of the opening position of the air introduction hole 95 to thereby eject the cleaning liquid in a pulsatile manner from the nozzle 93 or to atomize the cleaning liquid on the downstream side of the opening position of the air introduction hole 95 to eject the cleaning liquid in an atomized state from the nozzle 93 with the simple configuration of providing the air introduction hole 95 by appropriately setting the opening diameter D1 of the air introduction hole 95, the flow passage diameter (inner diameter) D2 of the ejection connection tube 92a, the ratio D1/D2 between the opening diameter of the air introduction hole 95 and the flow passage diameter of the ejection connection tube 92a, the flow rate of the air pump 97, the ejection pressure of the air pump 97, and the like.

Although the embodiment of the present invention has been described above, the present invention is not limited at all to the above embodiment. It is needless to say that the configuration thereof may be modified without departing from the gist of the invention.

REFERENCE SIGNS LIST

1 Oral cleaning device
2 Cleaning liquid tank
2a Side wall
3 Cleaning device body
4 Nozzle
4a Ejection port
4b Flange
4c Attachment portion
5 Seal ring
10 Casing
11 Support frame
12 Lower case
13 Upper case
14 Main body
14a Side wall
15 Support wall
16 Nozzle attaching recess
20 Ejection connection tube
21 Connection tubular portion
22 Seal ring
23 Supply pipe
23a Introduction port
30 Cleaning liquid supply passage
31 Mouth portion
31 Seal ring
32 Fitting recess
33 Fitting groove
34 Projection
35 Locking recess
36 Locking projection
37 Injection port
38 Lid
39 Seal ring
40 Power supply device
41 Induction coil
42 Circuit board
43 Secondary battery
44 Air pump
45 Power switch
46 Pump body
46a Ejection tube
47 Motor
48 Introduction connection tube
49 Air supply tube
50 Discharge connection tube
51 Air vent tube
51a Opening
52 Operation button
53 Valve body
54 Biasing means
55 Air vent passage
60 First check valve
61 Second check valve
62 First passage
63 Steel ball
64 Second passage
65 Steel ball
70 Pulsation means
71 Air introduction hole
72 Narrowing portion
80 Testing device
81 Acrylic plate
82 Silicone impression material
93 Abrasive film
90 Cleaning liquid ejection device
91 Cleaning liquid tank
92 Lid
92a Ejection connection tube
93 Nozzle
94 Supply pipe
95 Air introduction hole
96 Narrowing portion
97 Air pump

The invention claimed is:

1. An oral cleaning device, comprising:
an air-tightly closable cleaning liquid tank storing a cleaning liquid;
a cleaning liquid supply passage having an ejection port for ejecting the cleaning liquid into the oral cavity on one end and an introduction port open inside a bottom part of the cleaning liquid tank on the other end; and
an electric air pump supplying air into the cleaning liquid tank to pressurize the inside of the cleaning liquid tank,
wherein an air introduction hole is provided on a midway part of the cleaning liquid supply passage in the cleaning liquid tank, to open inside the cleaning liquid tank, the air pump is connected to the cleaning liquid supply passage only via the cleaning liquid tank,
wherein while part of the air supplied to the cleaning liquid tank from the air pump is supplied to the cleaning liquid supply passage through the air introduction hole, the cleaning liquid inside the cleaning liquid tank is supplied to the ejection port through the cleaning liquid supply passage by air pressure inside the cleaning liquid tank to thereby eject the cleaning liquid from the ejection port in a pulsatile manner.

2. The oral cleaning device according to claim 1, wherein the following four relational expressions are satisfied, where A (m/sec) denotes the flow velocity of the cleaning liquid in the cleaning liquid supply passage, D1 (mm) denotes the opening diameter of the air introduction hole with respect to the cleaning liquid supply passage, and D2 (mm) denotes the flow passage diameter of the cleaning liquid supply passage near an opening of the air introduction hole, $$3 \leq A \leq 40 \tag{1}$$

$$0.3 \leq D1 \leq 1.5 \tag{2}$$

$$1.5 \leq D2 \leq 5 \tag{3}$$

$$0.1 \leq D1/D2 \leq 0.5 \tag{4}.$$

3. The oral cleaning device according to claim 1, further comprising a narrowing portion projecting into the cleaning liquid supply passage to narrow the passage cross-sectional area, the narrowing portion being disposed at an opening position of the air introduction hole on the cleaning liquid supply passage.

4. The oral cleaning device according to claim 1, further comprising:
   an air vent passage opening the cleaning liquid tank to the atmosphere;
   a valve body capable of switching the air vent passage between an open state and a closed state;
   a power switch operating supply of power to the air pump; and
   a switch configured to switch the valve body to a closed state in response to an ON operation of the power switch and to an open state in response to an OFF operation of the power switch.

5. The oral cleaning device according to claim 4, further comprising a check valve preventing leakage of the cleaning liquid through the air vent passage when the oral cleaning device falls over, the check valve being disposed on a midway part of the air vent passage.

6. The oral cleaning device according to claim 1, wherein the air pump includes a rolling type air pump.

7. The oral cleaning device according to claim 1, wherein an ejection port side part of the cleaning liquid supply passage is composed of a nozzle, and the outermost diameter of the nozzle is set at 3 mm or more and 8 mm or less in a region to be inserted into the oral cavity.

\* \* \* \* \*